United States Patent [19]

Batzel et al.

[11] Patent Number: 4,900,817
[45] Date of Patent: Feb. 13, 1990

[54] MULTIRING PHTHALOCYANINE COMPOUNDS

[75] Inventors: Daniel A. Batzel, Cleveland Heights; Scott E. Rickert, Lakewood; Malcolm E. Kenney, Cleveland Heights, all of Ohio

[73] Assignee: Edison Polymer Innovation Corporation, Broadview Heights, Ohio

[21] Appl. No.: 200,746

[22] Filed: May 31, 1988

[51] Int. Cl.$^4$ .................. C09B 17/30; C09B 17/32
[52] U.S. Cl. .................... 540/128; 540/123; 540/139; 540/140; 540/145
[58] Field of Search ............ 540/123, 128, 139, 140, 540/145

[56] References Cited

U.S. PATENT DOCUMENTS

| | | | |
|---|---|---|---|
| 3,094,535 | 6/1963 | Kenney et al. | 260/314.5 |
| 3,094,536 | 6/1963 | Kenney et al. | 260/314.5 |
| 3,963,744 | 6/1976 | Smith et al. | 260/314.5 |
| 4,131,609 | 12/1978 | Wynne et al. | 260/314.5 |
| 4,132,842 | 1/1979 | Wynne et al. | 528/33 |
| 4,499,018 | 2/1985 | Doré et al. | 540/123 X |
| 4,638,286 | 1/1987 | Nichols | 338/34 |
| 4,648,992 | 3/1987 | Graf et al. | 540/124 |
| 4,725,525 | 2/1988 | Kenney et al. | 430/270 |
| 4,783,386 | 11/1988 | Nikles et al. | 540/128 X |
| 4,784,736 | 11/1988 | Lonsdal et al. | 540/145 X |
| 4,814,256 | 3/1989 | Aldug et al. | 540/128 X |

FOREIGN PATENT DOCUMENTS

245750A1 6/1984 Fed. Rep. of Germany.

OTHER PUBLICATIONS

S. Baker, et al.; IEE Proc., Part I:Solid-State Electron Devices, 1983, pp. 260–263.
A. W. Snow, et al., Natl. Sampe Tech. Conf., 1984, pp. 388–393.
G. G. Roberts, et al., Thin Solid Films, 1985, pp. 113–123.
Wohltjen, H. et al., *IEEE Transactions on Electronic Devices*, vol. ED-32, No. 7, Jul. 1985, pp. 1170–1173.

Primary Examiner—Richard L. Raymond
Attorney, Agent, or Firm—Oldham & Oldham

[57] ABSTRACT

Compounds are disclosed which comprise parallel, multiring, porphyrin-related compounds, particularly two-ring phthalocyanine compounds, which have a coordinating atom, either a metal or a metalloid, located at their center. The coordinating atoms in adjacent rings are connected by an oxygen bridge along an axial backbone disposed at right angles to the rings, and the coordinating atom and the ring on one end of the axis has a hydrophilic group attached thereto, while the coordinating atom in the ring at the other end of the axis has a hydrophobic group attached to it. Semiconducting films made from such compounds and devices made from such films, especially gas sensors, are also disclosed.

10 Claims, 2 Drawing Sheets

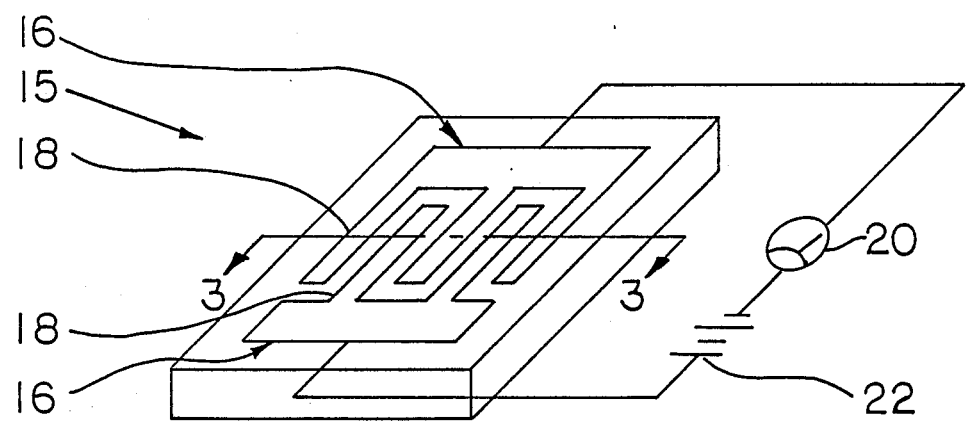
FIG. 2
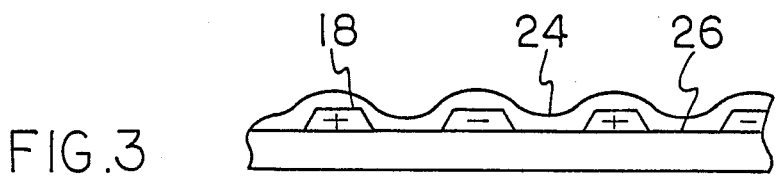
FIG. 3
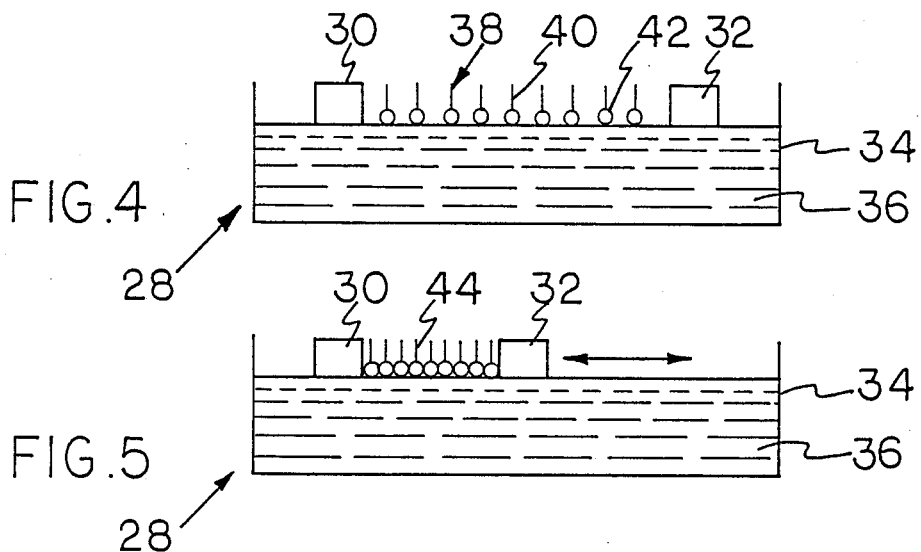
FIG. 4
FIG. 5

MULTIRING PHTHALOCYANINE COMPOUNDS

TECHNICAL FIELD

This invention relates to multiring phthalocyanine compounds and to their preparation and uses. More particularly, this invention relates to multiring phthalocyanine compounds useful in preparing films by the Langmuir-Blodgett, L-B, technique which can be employed in the fabrication of chemiresistor gas analyzers, and which are useful in various other microelectronic devices as well. Specifically, this invention relates to amphiphilic multiring phthalocyanines, especially two-ring phthalocyanine molecules which are axially interconnected at their centers, and which have a hydrophilic head group located at one end of the interconnecting axis, and a hydrophobic tail group at the other end of the axis.

BACKGROUND OF THE INVENTION

Chemiresistors are devices which have the electrical characteristics of a resistor whose conductivity is modulated by the nature of the various chemical species with which they are in contact. Since the devices are both uncomplicated and sensitive to their environment, they have substantial potential applications both in detection, and in process control. Basically, chemiresistors comprise electrodes in contact with a semiconductor film. During use, a small voltage is supplied to the electrodes, generating a current whose magnitude depends upon the conductivity of the film, the latter in turn depending upon the nature of the ambient chemical substances with which the film is in contact.

Although the electrical conductivities of metal oxide semiconductors are detectably influenced by gases and vapors contacting their surfaces, they suffer from the fact that the heat required to operate them requires substantial power to produce, as well as from the fact that they lack sufficient sensitivity to discriminatingly detect the presence of very dilute materials.

The shortcomings of the metal oxide semiconductors has led to considerable interest in finding satisfactory organic semiconductors. While it has long been known that the conductivity of certain organic films is affected by the chemical substances with which they are in contact, the extreme sensitivity of the films to degradation has been a problem. Furthermore, the conductivity of many such films is not high, which makes it difficult to measure differences resulting from contacted substances sufficiently accurately.

Metal-substituted phthalocyanines are an exception, however, since they are capable of achieving acceptable conductivities, and in addition, such compounds do not tend to decompose readily even at elevated temperatures. Films of copper tetracumylphenoxy phthalocyanine, for example, have been formed and deposited on electrode quartz substrates to prepare gas detection chemiresistor devices.

While such phthalocyanine compounds can be used in conjunction with L-B techniques, they tend to suffer from the hydrophobic nature of their ring structure. As will be more fully explained in the following, the Langmuir-Blodgett technique consists of depositing a film-forming material on a water surface, compressing the molecules of the material together to form a compact monomolecular film, and then passing the object to be coated through the film, causing adherence of the film to the object. In the case of the phthalocyanines, the hydrophobic nature of the ring structure strongly resists deployment of the rings parallel to the surface of the water, the rings preferring to orient themselves on their edges, which results in their disposition on the surface of the water at an angle other than 0°. Since the rings of the molecules are compressed together during the film-forming procedure, the rings tend to overlay each other, a configuration maintained during the subsequent coating process. The overlayed condition of the rings makes it impossible for the topmost molecules comprising the coating to fully present their gas-sensitive rings to the ambient environment, seriously impairing their detection capabilities.

In an effort to overcome this problem, hydrophilic side groups have sometimes been substituted along the periphery of the rings. While such expedients allow disposition of the rings parallel to the surface of the water, the side groups tend to interfere with the necessary L-B compression step, leaving voids in the film. Such voids both weaken the film and interfere with the electrical function of the chemiresistor sensor chips made therefrom.

Other methods which have been suggested for preparing coating films include spin-coating, as well as sublimation processes. These also suffer from a number of drawbacks, however, including the fact that films so formed are relatively thick, and they also tend to lack uniformity. In order to be successful in chemiresistor applications, it is imperative that the coating films be uniform to avoid variations in their electrical characteristics. In addition the films must be as thin as possible in order to allow the detected substances to be adsorbed rapidly and to be driven off rapidly by heating during the regeneration cycle.

DESCRIPTION OF THE INVENTION

In view of the preceding, it is a first aspect of this invention to provide multiring porphyrin-related compounds useful for the fabrication of microelectronic devices, and for other applications.

A second aspect of this invention is to make available multiring phthalocyanine compounds which can be coated on substrates in such a way that the planes of their ring structures are parallel to the surface of the substrate on which the coating is placed.

Another aspect of this invention is to furnish a phthalocyanine compound in which two, parallel phthalocyanine rings are interconnected along an axis passing through their centers, and in which a hydrophobic group is attached to the unconnected side of the center of one of the rings, while a hydrophilic group is attached to the unconnected side of the other ring's center.

An additional aspect of this invention is to provide a multiring phthalocyanine compound whose electrical properties are affected by the nature of the ambient chemicals with which it is in contact, and which is particularly useful in fabricating electronic devices for detecting ambient gases and vapors.

A further aspect of this invention is to provide an organic gas sensor coating film which exhibits an increased resistance to film-disorienting collapse during the film compression step of the Langmuir-Blodgett film preparation technique, and which is physically strong enough to be formed into multiple layers of film on a substrate.

The foregoing and other aspects, as will be more fully explained in the following, detailed description of the invention, are provided by a multiring compound in which a plurality of adjacent, parallel porphyrin-related rings having a coordinating atom comprising a metal or a metalloid atom located at the center of said rings are interconnected along an axis perpendicular to the surface of said rings and passing through the center thereof, by means of an oxygen atom located along said axis, said oxygen atom connecting the coordinating atoms in adjacent rings, and in which the outermost ring at a first end of said axis has a hydrophilic group attached to the coordinating atom thereof, while the outermost ring at the other end of said axis has a hydrophobic group attached to the coordinating atom thereof.

The foregoing and additional aspects of the invention are provided by the process of forming a film from the compound of the preceding paragraph by means of a Langmuir-Blodgett balance and coating a substrate with multiple layers of said film.

The foregoing and still further aspects of the invention are provided by a two-ring phthalocyanine compound in which two adjacent, parallel phthalocyanine rings having a coordinating atom comprising a metal or metalloid atom located at the center of said rings, are interconnected along an axis perpendicular to the surface of said rings and passing through the center thereof, by means of an oxygen atom connecting said coordinating atoms, and in which one of said rings has a hydrophilic group attached to the coordinating atom thereof, while the other of said rings has a hydrophobic group attached to the coordinating atom thereof.

The foregoing and yet additional aspects of the invention are provided by a process of fabricating a gas sensor by forming a film from the compound of the preceding paragraph by means of a Langmuir-Blodgett balance and coating a planar microelectrode array with multiple layers thereof.

BRIEF DESCRIPTION OF THE DRAWINGS

The invention will be better understood when reference is had to the following drawings, in which like numbers refer to like parts, and in which

FIG. 2 is an isometric representation of a sensor chip of the type with which the films produced from compounds of the invention are useful.

FIG. 3 is a partial cross-sectional view of the sensor chip of FIG. 2, along line 3—3 of that Figure.

FIG. 4 is a representational illustration of a Langmuir-Blodgett balance after a solution of a compound of the invention has been deposited on the subphase thereof.

FIG. 5 shows the representational illustration of the Langmuir-Blodgett balance of FIG. 4, following compression of the monomolecular layer to a quasi-solid.

DETAILED DESCRIPTION OF THE INVENTION

Figure 1:
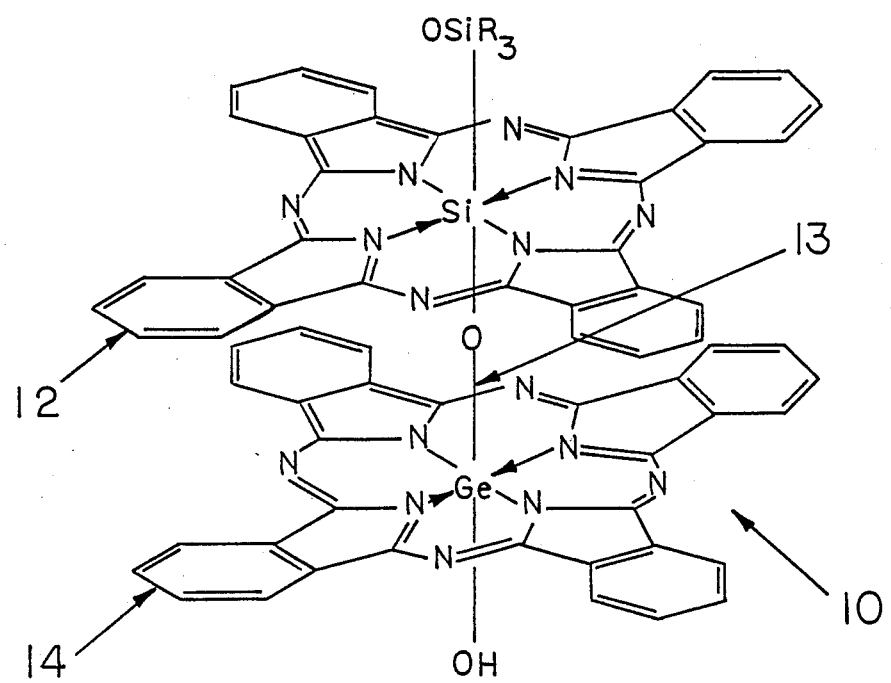
FIG. 1 is a three-dimensional representation of the structure of a compound comprising one embodiment of the invention.

FIG. 1 is a three-dimensional representation of the structure of one of the compounds of the invention, generally 10. As shown, compound 10 consists of two phthalocyanine rings, an upper ring 12, and a lower ring 14, connected along a "backbone" axis 13. The upper ring has a silicon coordinating atom at the center thereof, while the lower ring has germanium as its center coordinating atom. The coordinating atoms in the two rings are connected or "bridged" by an oxygen atom, and the axis, which is located at right angles to the surface of the rings contains a hydrophilic hydroxyl atom attached to the coordinating atom of the lower ring 14, and a hydrophobic triorganosiloxy group connected to the coordinating atom of the upper ring 12. Any of various porphyrin-related compounds may be employed in producing films of the type contemplated by the invention, including porphine compounds, naphthalocyanine compounds, the phthalocyanine compound of the figure, and others. The porphyrin-related phthalocyanine compound illustrated in the figure is one of those particularly preferred, however, for reasons including the ease of synthesis, as well as its thermal, chemical, and photochemical stability.

As previously referred to, it is important that molecules used in Langmuir-Blodgett balances to form coating films be capable of orienting their detecting molecules parallel to the subphase used to form the film so that in the subsequent dip-coating procedure, the detecting molecules will maintain their alignment parallel to the substrate surface on which they are placed, thus allowing maximum exposure of the topmost detecting molecules. As can be seen from the figure, the axial backbone accomplishes this by providing a hydrophilic group on its lower side, in effect serving as a means to vertically orient the axis, due to the attraction of the hydroxyl group for the aqueous subphase. The hydrophobic group, on the other hand, serves to supplement the desired orientation, as well as enhancing the solubility in the organic solvent required to prepare the solution of the molecule required for its deposition on the subphase.

The multiring structure is provided in order to increase the collapse pressure of the molecule during the compression step required to prepare a Langmuir-Blodgett film. During the compression step, the deposited molecules are forced together until their peripheries are substantially contiguous so that a void-free film is obtained. When the pressure reaches a particular point, specific for each particular type molecule, referred to as the "collapse pressure", some of the molecules begin to be forced under their adjacent neighbors, a phenomenon leading to undesirable molecular disorder. The provision of the vertically oriented, multiring stacks contemplated by the invention increases the collapse pressure of the molecules, making it much easier to form the necessary monomolecular films.

Generally speaking, the greater the number of rings present, the higher and better the collapse pressure. In addition, the conductivity effects produced by environmental contacts are enhanced due to the fact that it is believed conductivity occurs as a result of electron transfer from ring to adjacent ring. Since the electrons cannot easily pass the axial hydrophilic and hydrophobic end groups, or "caps", it is desirable that the ratio of rings to caps be as high as possible. The problems of synthesis increase, however, as the number of rings increase, and it has been found relatively impractical to produce compounds having more than about 10 rings in a compound's stack, and it is preferred that from 2 to about 5 rings be used.

The coordinating atoms employed in the rings may either be metals, for example, tin, and the like, or the so-called metalloids, such as silicon and germanium. The coordinating atoms, each of which is connected to the adjacent coordinating atom by the oxygen bridge previously referred to, may be identical or different. Stated differently, while the figure shows a silicon atom bridged by oxygen to germanium, two germanium atoms could be thus bridged, or two silicon atoms, the same principle applying to stacks containing more than the two rings shown.

Attempts have been made to achieve parallel orientation through the use of ring compounds in which the peripheries of the rings have been substituted with hydrophilic groups. However, the peripheral groups interfere with concentration of the molecules in the compression step, interference of the groups tending to leave voids in the film. The voids in turn, interfere with proper contact of the rings with the substances to be detected; consequently, avoidance of any need to provide such peripheral substitution constitutes one of the notable advantages of the compounds of the invention.

The hydrophobic groups which form part of the compounds of the invention may be any of a wide variety of compounds, for example, aryl, arylalkyl, or alkyl, and they may be of the organic, or organometallic type. The use of groups containing from about 10 to 30 carbon atoms has been found to confer the necessary solubilizing characteristics on the compounds, and to assist the orientation function of the hydroxyl group at the other end of the axial backbone, due to the hydrophobicity resulting from that number of carbon atoms. The use of groups similar to the trihexylsiloxy group shown has been found to be particularly beneficial, and such groups are, therefore, preferred.

The hydrophilic groups useful in the invention include groups containing at least one hydroxyl group including polyol groups, various acid groups, including the salicylate group, as well as other hydrophilic groups.

FIG. 2 is an isometric representation of a sensor chip, generally 15, sometimes employed in connection with films formed from compounds of the invention. The sensor chip 15 includes microelectrode arrays, generally 16, comprising interdigitated electrode fingers 18. The arrays 16 are coated with a film of the type contemplated by the invention, better seen in FIG. 3, and are connected to an ammeter 20, and to a power source, usually a battery, 22. Contact of the film with various gases or vapors in the environment causes the conductivity of the film to vary, and therefore, varying current to flow in the device. The particular configuration of the electrodes, which may be made from silver, gold, vapor deposited aluminum, or similar materials, is relatively unimportant, and a variety of such devices are known to the art. In addition, permittivity rather than current flow may be used to determine the amount of the detected substance present.

The films contemplated by the invention may also be used in a wide variety of microelectronic devices other than gas sensors, including electroluminescent diodes, bistable switches, photovoltaic and electrochromic devices, and others.

FIG. 3 is a partial cross-sectional view of the sensor chip 15 of FIG. 2 along line 3—3 of that figure, showing the insulating substrate 26 on which the interdigitated electrode fingers 18 are located, coated by a semiconductor film 24 of the invention. Dielectric films of the invention typically exhibit relative permittivities in the order of 5.5, and it is theorized that the conduction exhibited by the rings in the molecules is a "hopping-type" mechanism. The electrical characteristics of the films are temperature dependent and specific for the ambient substances detected. In other words, for each contacted substance, at a given temperature the films exhibit a specific conduction profile, allowing determination of the presence of such substances by comparisons of detection conductivity values with empirical calibrations.

FIG. 4 is a representational illustration of a Langmuir-Blodgett balance, generally 28, after a solution of a compound of the invention has been deposited on the subphase 36, water, thereof.

The figure shows the subphase 36 contained in a trough 34. A solvent solution of the compound of the invention, generally 38, the compound including a hydrophobic end 40 and a hydrophilic end 42, is deposited between a stationary floating barrier 30 and a moving barrier 32. After deposition of the compound, the solvent is allowed to evaporate, typically requiring no more than about 5 minutes, and the moveable barrier 32 is moved towards the stationary barrier 30, compacting the molecules so that the edges of the rings are contiguous with the edges of adjacent rings.

FIG. 5 shows the representational illustration of the Langmuir-Blodgett balance of FIG. 4, following compression of the monomolecular layer to a quasi-solid. In the figure, the subphase 36 contained in trough 34 of the balance 28 contains a close packed film 44 of the molecules of the invention, compressed between stationary barrier 30 and moveable barrier 32, the latter being moveable in the direction of the associated arrow. While the amount of solution to be deposited on the subphase 36 may be varied, depending upon the dimensions of the balance, it is necessary that there be enough to result in a sufficient area for substrate dipping after the molecules have been compressed, but not so much that the molecules overlap each other. In addition, it is important that the water comprising the subphase be rigorously purified to eliminate foreign materials which could disrupt the continuity of the film, or undesirably alter its physical character.

Figure 6:
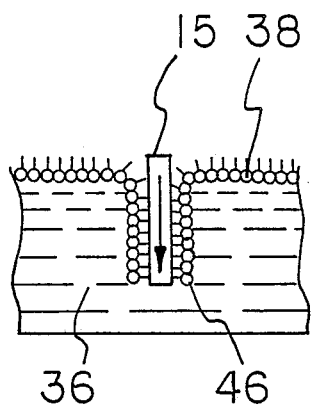
FIG. 6 is a partial view of a compressed monomolecular Langmuir-Blodgett film of the type representationally illustrated in FIG. 5 into which a substrate to be coated has been inserted.

FIG. 6 is a partial view of a compressed monomolecular Langmuir-Blodgett film of the type representationally illustrated in FIG. 5 into which a substrate to be coated has been inserted. The figure shows a sensor chip substrate 15 being inserted downwardly through the monomolecular film of the compound of the invention 38 floating on the water subphase 36. As the substrate is inserted, the film adheres thereto, providing a first film layer 46 of the desired coating. The figure presupposes the surface of the substrate to be of a hydrophobic character.

Figure 6A:
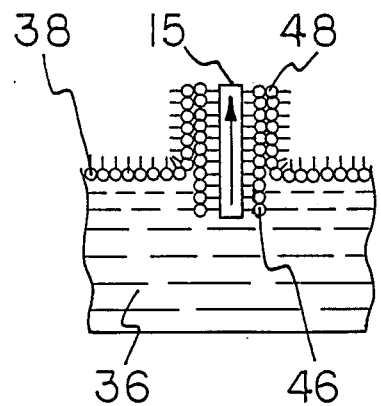
FIG. 6A shows the withdrawal of the inserted substrate of FIG. 6.

FIG. 6A shows the withdrawal of the inserted substrate of FIG. 6. As the substrate 15 is withdrawn from the subphase 36, a second film layer 48 is coated on the top of the first film layer 46. As might be inferred from the descriptions of FIG. 6, if the surface of the substrate were hydrophilic in character, it would repel the film during insertion, in which case the first film layer would only be deposited during the withdrawal step. In any event, the process of sequentially inserting and withdrawing the substrate is continued a sufficient number of times to deposit the thickness of coating desired, ordinarily from about 60 to 500 angstrom units, equivalent to about 5 to 45 layers of the compound of FIG. 1.

The following examples, while not intended to be limiting in nature, are illustrative of the invention.

EXAMPLE 1

Synthesis of the compound of FIG. 1, (HO)GePcOSiPc(OSi(n—$C_6H_{13}$)$_3$) in which Pc represents a phthalocyanine ring. Some of the procedures used in the synthesis are carried out with protection from light. These are indicated by the designation (p).

Under argon, 5.69 gms of $CH_3GeCl_3$ are mixed with 7.64 gms of diiminoisoindoline and 60 mLs of distilled, deoxygenated quinoline. The mixture is heated to reflux for 30 minutes (p), refluxed for 1 hour (p), cooled (p), and filtered (p). The solid is washed with methanol, air-dried and weighed to yield 5.64 gms.

22.7 gms of the product prepared by the above procedure are mixed with 600 mLs of concentrated sulfuric acid, and the mixture formed is maintained at 0° C. while being stirred (p). The resulting solution is poured over 1500 gms of ice (p), and the suspension thus obtained is filtered. The solid is then washed with water, followed by a 1:1 mixture of warm (about 50° C. concentrated ammonium hydroxide-pyridine solution in a separate vessel with stirring, and finally by a 2:5 ethanol-water solution, also in a separate vessel with sonication. The resulting material is air-dried and weighed, yielding 20.6 gms. A mixture of 3.60 gms of the latter product is then refluxed for 1 hour (p) with 250 mLs of toluene and 3.51 gms of HOSi(n—$C_6H_{13}$)$_3$, following which it is filtered (p). The residue is washed with toluene (p), and the washings and the filtrate are combined and vacuum evaporated at about 85° C. to produce a viscous suspension (p). The suspension is thereafter mixed with 50 mLs of pentane (p), and the resulting mixture is cooled to 0° C. (p), and filtered (p). The solid thus obtained is vacuum dried at about 85° C., and weighed, yielding 3.69 gms of product.

1.50 gms of the latter solid product is mixed with 3 mLs of glacial acetic acid, 3 mLs of water, and 50 mLs of toluene (p), and the suspension formed is refluxed for 30 minutes (p) and filtered (p). The solid is thereafter washed with methanol, air dried, and mixed with 5 mLs of concentrated ammonium hydroxide and 50 mLs of pyridine. The resulting suspension is refluxed for 15 minutes and filtered. After being washed with methanol, the solid is vacuum dried at about 85° C. and weighed to produce 0.814 gm of product.

2.17 gms of the latter product are mixed with 3.15 gms of SiPc(OH) (OSi(n—$C_6H_{13}$)$_3$), and suspended in 150 mLs of 1,2,4-trimethylbenzene, following which the suspension is refluxed for 4 hours (p) and filtered (p). The residual solid is washed with toluene (p) and the washings and filtrate are combined (p) and vacuum evaporated at about 70° C. to provide a viscous suspension (p). The suspension is mixed with 100 mLs of pentane, filtered, and the solid is vacuum dried at about 85° C. and weighed to give 3.91 gms of product.

3.14 gms of the latter product are then dissolved in 3 Ls of toluene and the solution formed irradiated with direct sunlight for 75 minutes before being vacuum evaporated at about 30° C. to dryness. The solid remaining is vacuum dried at about 85° C. and weighed to yield 2.77 gms. (HO)GePcOSiPc(OSi(n—$C_6H_{13}$)$_3$) is separated from the product thus obtained by column chromatography. The separated compound is deep blue, soluble in chloroform, and slightly soluble in toluene and pyridine.

A monomolecular film is subsequently prepared using the Langmuir-Blodgett film balance and the procedures previously described. The procedure involves a solution of (HO)GePcOSiPc(OSi(n—$C_6H_{13}$)$_3$) in a high pressure liquid chromotography, HPLC, grade chloroform, with 0.75% ethanol. The concentration of the solution is about $10^{-3}$ molar, about 1.4 mg/mL. The films are prepared by spreading about 35 microliters of the solution, about $10^{-8}$ moles, on the water, using a Drummond micropipetter at an initial area of about 2.0 nanometer$^2$/molecule. After 4 to 5 minutes the resulting film is compressed to a pressure of 10 mN/m.

The substrate used is an interdigitated microelectronic device equipped with temperature scanning ability. The device is ultrasonically cleaned for 15 to 30 minutes with HPLC grade methanol, flushed with ultrapure water, and dried at 120° C. in an oven.

In the monolayer deposition process, the device is mounted in the film balance with its long axis perpendicular to the surface of the water, and then is repeatedly submerged and withdrawn from the water until a 50-layer film of (HO)GePcOSiPc(OSi(n—$C_6H_{13}$)$_3$) has been deposited on the device. The change in conductivity of the film is then measured over a temperature range of from about 20° C. to 180° during exposure to nitrogen dioxide in nitrogen, and subsequently to chlorine in nitrogen.

At a nitrogen dioxide concentration in nitrogen of about $10^2$ ppm, the conductivity increases from a measurable fraction of a milliohm/centimeter. A similar result is obtained for about $10^2$ ppm of chlorine in nitrogen. No film aging or significant hysteresis for cycling temperature, forward or backward, is observed.

EXAMPLE 2

In another experiment designed to provide a different hydrophobic endcap, a mixture of HOSiPcCH$_3$ and HOSi(CH$_3$)$_2$n—$C_{18}H_{37}$, having a mole ratio of 1:2, is prepared in xylene and refluxed for about 1 hour before being evaporated to dryness under vacuum. The residue is then dissolved in wet toluene, and the solution is photolyzed in direct sunlight for about 1 hour, after which it is evaporated to dryness under vacuum to give HOSiPcOSi(CH$_3$)$_2$n—$C_{18}H_{37}$. Using a procedure like that of Example 1, in which, however, HOSiPcOSi(CH$_3$)$_2$n—$C_{18}H_{37}$ is used in place of SiPc(OH)(OSi(n—$C_6H_{13}$)$_3$), the compound HOGePcOSiPcOSi(CH$_3$)$_2$n—$C_{18}H_{37}$ is obtained.

EXAMPLE 3

A hydrophilic endcap is incorporated by mixing (HO)GePcOSiPc(OSi(n—$C_6H_{13}$)$_3$) with SiCl$_4$, and Et$_3$N in a mole ratio of about 1:10:20 in toluene. The solution is heated gently for several hours, and then evaporated to dryness under vacuum. The residue is treated with an excess of a pyridine-water solution, in about a 1:3 volume ratio, washed with water and dried, yielding (HO)$_3$SiOGePcOSiPcOSi(n—$C_6H_{13}$)$_3$.

EXAMPLE 4

Still another compound having a different hydrophilic endcap is prepared by a procedure involving mixing (HO)GePcOSiPc(OSi(n—$C_6H_{13}$)$_3$) and C(CH$_2$OH)$_4$, in a mole ratio of about 1:100, in sufficient dimethylformamide to dissolve the solid material present. The mixture is then heated gently for about 2 hours, diluted with excess water, and filtered. The solid thus isolated is washed with water and vacuum dried to provide (HOCH$_2$)$_3$CCH$_2$OGePcOSiPcOSi(-n—C$_6$H$_{13}$)$_3$.

EXAMPLE 5

A 3-ring stack is prepared by mixing (HO)GePcOSiPc(OSi(n—C$_6$H$_{13}$)$_3$) with HOSiPcCH$_3$ in about a mole ratio of 1:1 with sufficient 1,2,4-trimethylbenzene to provide a dilute suspension. The suspension is then refluxed for several hours, filtered, and evaporated to dryness under vacuum. The residue is chromatographed on alumina with toluene as an eluant, and then dissolved in a large amount of wet toluene, before being photolyzed in direct sunlight for about 1 hour. The resulting suspension is evaporated to dryness under vacuum to produce HOSiPcOGePcOSiPcOSi(n—C$_6$H$_{13}$)$_3$.

EXAMPLE 6

Another 3-ring compound, HOGePcOGePcOSiPcOSi(n—C$_6$H$_{13}$)$_3$, is prepared by forming a mixture of (HO)GePcOSiPc(OSi(n—C$_6$H$_{13}$)$_3$) with HOGePcCH$_3$, the two materials being present in a mole ratio of about 1:1, in the presence of sufficient 1,2,4,-trimethylbenzene to provide a dilute suspension. The suspension is then refluxed for several hours, filtered, and evaporated to dryness under vacuum. The residue is chromatographed on alumina with toluene as an eluent, and then dissolved in a large amount of wet toluene, before being photolyzed in direct sunlight for about 1 hour. The resulting suspension is evaporated to dryness under vacuum and the residue purified to give the desired product.

EXAMPLE 7

A compound having an axial backbone of SiOSi is prepared by a procedure like that described in connection with Example 1, in which, however, CH$_3$SiCl$_3$ is used in place of CH$_3$GeCl$_3$, thereby producing HOSiPcOSiPcOSi(n—C$_6$H$_{13}$)$_3$.

EXAMPLE 8

While it is generally desirable to avoid substituting the peripheral portions of the ring, since the substituents interfere with the compression step as previously described, relatively small substituents may be used without detrimental effect, as shown in the following example in which HOGePcCl$_4$OSiPcOSi(n—C$_6$H$_{13}$)$_3$ is prepared by a procedure which involves formation of a suspension of 4-chlorophthalonitrile and a small amount of NaOCH$_3$ in sufficient methanol to provide a solution. A stream of ammonia is passed through the solution at room temperature for about 1 hour, and then at reflux for about 3 hours. The mixture is filtered to give 4-chlorodiiminoisoindoline. Subsequently, using a procedure like that of Example 1, in which, however, the latter compound is used in place of diimiinoisoindoline, HOGePcCl$_4$OSiPcOSi(n—C$_6$H$_{13}$)$_3$ is obtained.

EXAMPLE 9

In a still further experiment in which a porphyrin ring is used in place of the phthalocyanine ring, a mixture of porphine and CH$_3$GeCl$_3$, combined in mole ratio of 1:1, is dissolved in 1,2,4-trimethylbenzene and refluxed for about 3 hours before being evaporated to dryness under vacuum. The residue is refluxed with dilute sodium hydroxide for about 2 hours, and washed with water to give HOGePCH$_3$, in which P represents porphine. Thereafter, using a procedure like that of Example 1, in which, however, the HOGePCH$_3$ is used in place of the HOGePcCH$_3$ formed as an intermediate, and HOGePOSiPcOSi(n—C$_6$H$_{13}$)$_3$ is obtained.

While in accordance with the patent statutes, a preferred embodiment and best mode has been presented, the scope of the invention is not limited thereto, but rather is measured by the scope of the attached claims.

What is claimed is:

1. A multiring compound containing from 2 to about 10 rings in which a plurality of adjacent, parallel porphyrin-related rings each selected from the group consisting of porphyrin, substituted porphyrin, phthalocyanine and substituted phthalocyanine rings and having a coordinating atom which is a metal or a metalloid atom located at the center of said rings, are interconnected along an axis perpendicular to the surface of said rings and passing through the center thereof, by means of an oxygen atom located along said axis, said oxygen atom connecting the coordinating atoms in adjacent rings, and in which the outermost ring at a first end of said axis has a hydrophilic group attached to the coordinating atom thereof, while the outermost ring at the other end of said axis has a hydrophobic group attached to the coordinating atom thereof.

2. A compound according to claim 1 in which from at least two to about five rings are so interconnected.

3. The compound of claim 1 in which said coordinating atoms, which may be the same or different, are selected from the group consisting of silicon, germanium, and tin.

4. A two-ring phthalocyanine compound in which two adjacent, parallel phthalocyanine rings having a coordinating atom which is a metal or a metalloid atom located at the center of said rings, are interconnected along an axis perpendicular to the surface of said rings and passing through the center thereof, by means of an oxygen atom connecting said coordinating atoms, and in which one of said rings has a hydrophilic group attached to the coordinating atom thereof, while the other of said rings has a hydrophobic group attached to the coordinating atom thereof.

5. A compound according to claim 4 in which one of said coordinating atoms is silicon, and the other is germanium.

6. A compound according to claim 4 wherein said hydrophilic group contains at least one hydroxyl group and said hydrophobic group is an organic group or organometallic group containing from about 10 to 30 carbon atoms.

7. A compound according to claim 6 in which said hydrophobic group is a trialkylsiloxy group in which the alkyl radical may be the same or different.

8. The compound of claim 6 in which said hydrophobic group is a trihexylsiloxy group.

9. A multiring compound containing from 2 to about 10 adjacent, parallel phthalocyanine rings, each having a coordinating atom selected from the group consisting of silicon and germanium located at the center of said ring, wherein said rings are interconnected along an axis perpendicular to the surface of said ring and passing through the center thereof, by means of an oxygen atom located along said axis, said oxygen atom connecting the coordinating atoms in adjacent rings, and in which the outermost ring at a first end of said axis has a hydrophilic group attached to the coordinating atom thereof, while the outermost ring at the other end of said axis has a hydrophobic group attached to the coordinating atom thereof.

10. A compound according to claim 9 wherein said hydrophilic group contains at least one hydroxyl group and said hydrophobic group is an organic group or organometallic group containing from about 10 to 30 carbon atoms.

* * * * *